(12) United States Patent
Patel

(10) Patent No.: US 8,906,052 B1
(45) Date of Patent: Dec. 9, 2014

(54) METHOD AND DEVICE FOR THE TREATMENT OF HYPERTROPHIC CARDIOMYOPATHY

(75) Inventor: Vinod Patel, Tampa, FL (US)

(73) Assignee: University of South Florida, Tampa, FL (US)

( * ) Notice: Subject to any disclaimer, the term of this patent is extended or adjusted under 35 U.S.C. 154(b) by 569 days.

(21) Appl. No.: 12/776,884

(22) Filed: May 10, 2010

Related U.S. Application Data

(60) Provisional application No. 61/176,738, filed on May 8, 2009.

(51) Int. Cl.
*A61B 17/32* (2006.01)
*A61B 17/22* (2006.01)
*A61B 19/00* (2006.01)

(52) U.S. Cl.
USPC ............................ 606/170; 606/159; 128/898

(58) Field of Classification Search
USPC ......... 606/108, 158, 159, 167, 170, 171, 180, 606/198; 604/22; 128/898
See application file for complete search history.

(56) References Cited

U.S. PATENT DOCUMENTS

| | | | |
|---|---|---|---|
| 5,059,203 A * | 10/1991 | Husted | 606/159 |
| 5,106,386 A | 4/1992 | Isner et al. | |
| 5,507,795 A * | 4/1996 | Chiang et al. | 606/167 |
| 5,665,062 A * | 9/1997 | Houser | 604/22 |
| 5,910,150 A * | 6/1999 | Saadat | 606/159 |
| 5,947,983 A * | 9/1999 | Solar et al. | 606/144 |
| 6,027,514 A * | 2/2000 | Stine et al. | 606/159 |
| 6,206,898 B1 * | 3/2001 | Honeycutt et al. | 606/159 |
| 6,398,795 B1 * | 6/2002 | McAlister et al. | 606/139 |
| 6,447,525 B2 * | 9/2002 | Follmer et al. | 606/159 |
| 6,732,739 B2 | 5/2004 | Cosgrove | |
| 2003/0032936 A1 | 2/2003 | Lederman | |
| 2007/0021740 A1 | 1/2007 | Weber | |
| 2007/0207473 A1 | 9/2007 | Ackerman et al. | |

* cited by examiner

*Primary Examiner* — Tuan V Nguyen
(74) *Attorney, Agent, or Firm* — Nilay J. Choksi; Jeremy Spier; Smith & Hopen, P.A.

(57) ABSTRACT

A method and device for the treatment of hypertrophic cardiomyopathy. The device includes a cutting device for resection of a thickened myocardium. The operator positions the cutting device adjacent to the myocardium that is to be resected and then slides a tubular blade within an outer shell of the cutting device to resect the septum.

10 Claims, 4 Drawing Sheets

METHOD AND DEVICE FOR THE TREATMENT OF HYPERTROPHIC CARDIOMYOPATHY

CROSS-REFERENCE TO RELATED APPLICATIONS

This application claims priority to U.S. Provisional Patent Application No. 61/176,738, entitled "PATEL'S SEPTAL MYECTOMY DEVICE", filed on May 8, 2009, the contents of which are hereby incorporated by reference.

BACKGROUND OF THE INVENTION

1. Field of the Invention

This invention relates to a method and device for the treatment of hypertrophic cardiomyopathy. More specifically, this invention relates to a method and device that retracts the thickened myocardium.

2. Description of the Prior Art

Hypertrophic cardiomyopathy (HCM) is a complex type of heart disease that affects the heart muscle. It causes thickening of the heart muscle (especially the ventricles, or lower heart chambers), left ventricular stiffness, mitral valve changes, and cellular changes.

Thickening of the heart muscle (myocardium) occurs most commonly at the septum. The septum is the muscular wall that separates the left and right side of the heart. Problems occur when the septum between the heart's lower chambers, or ventricles, is thickened. The thickened septum may cause a narrowing that can block or reduce the blood flow from the left ventricle to the aorta—a condition called "outflow tract obstruction." The ventricles must pump harder to overcome the narrowing or blockage. This type of hypertrophic cardiomyopathy may be called hypertrophic obstructive cardiomyopathy (HOCM).

HCM may also cause thickening in other parts of the heart muscle, such as the bottom of the heart called the apex, right ventricle, or throughout the entire left ventricle.

Stiffness in the left ventricle occurs as a result of cellular changes that occur in the heart muscle when it thickens. The left ventricle is unable to relax normally and fill with blood. Since there is less blood at the end of filling, there is less oxygen-rich blood pumped to the organs and muscles. The stiffness in the left ventricle causes pressure to increase inside the heart.

The narrowing of the left ventricular outflow tract disrupts the proper function of the mitral valve, resulting in outflow obstruction and increased pressure in the left ventricle. The obstruction is the result of the mitral valve striking the septum. When this occurs, the mitral valve frequently leaks, causing the blood to go back into the left atrium.

HCM is a genetic disease with an autosomal dominant pattern of inheritance and affects an estimated 600,000 to 1.5 million Americans, or one in 500 people. This disease entity carries annual rates of heart failure, death, or transplantation of 0.55% and stroke-related deaths of 0.07%. HCM is the most common cause of sudden cardiac death in people under the age of 30.

Symptoms associated with the presence of ventricular tachycardia or heart failure include chest pain, shortness of breath and fatigue, syncope, and palpitation.

Regardless of the presence of symptoms, significant outflow tract obstruction at rest is an independent predictor of poor prognosis in patients with HCM. After adjusting for age, gender, heart failure at entry, presence of atrial fibrillation, and LV wall thickness ≥30 mm, patients with obstruction had a high rate of HCM-related mortality (relative risk 1.6, 95% CI 1.1-2.4).

Patients with obstructive HCM who are severely symptomatic (e.g., New York Heart Association functional class III or IV) or have recurrent syncope despite pharmacologic therapy are candidates for cardiac surgery called septal myectomy. During this surgical procedure, the surgeon removes a small amount of the thickened septal wall (approximately 3 to 15 g) to widen the outflow tract (the path the blood takes) from the left ventricle to the aorta. Myectomy is considered when medications are not effective in treating HCM. Peri-operative mortality varies from 0.7-6.0%. Excessive resection of muscle can cause a ventricular septal defect, a serious complication that may occur in up to 2% of patients. Other complications include inadequate intraoperative protection of the hypertrophied muscle against ischemia, causing LV dysfunction at a later date, damage to the aortic valve, causing aortic regurgitation subsequently requiring aortic valve replacement, and development of left bundle branch block (LBBB) or complete heart block (CHB) requiring a permanent pacemaker which occurs postoperatively in approximately 5 to 10% of patients.

Nonsurgical septal reduction therapy (NSRT), also called transcoronary ablation of septal hypertrophy (TASH) or ethanol septal ablation, consists of infarction and thinning of the proximal interventricular septum via infusion of ethanol into the first septal perforating branch of the left anterior descending coronary artery through an angioplasty catheter thereby reducing the size of the septum. Ethanol septal ablation in patients with HCM has been complicated by ECG changes, including transient QT prolongation, Q waves, right bundle branch block, and complete heart block (14-25%). Other more serious complications include ventricular tachyarrhythmias, arrhythmic death, and, although infrequent when performed by experienced operators, a large myocardial infarction caused by escape of ethanol from the target vessel. Another concern has been that subsequent scarring might increase the long-term incidence of ventricular arrhythmias, bradyarrhythmias, and heart failure.

It is therefore an objective of the present invention to eliminate the need for invasive septal myectomy surgery and the significant morbidity and mortality associated with open heart surgery complications, such as temporarily stopping blood flow through the heart.

It is yet another objective of the present invention to eliminate the serious and lethal complications of noninvasive septal ablation done via catheters.

SUMMARY OF INVENTION

The long-standing but heretofore unfulfilled need for an improved method and device for treatment of HCM is now met by a new, useful, and nonobvious invention.

The proposed technique is non surgical, allowing use of mild, local anesthetics, as opposed to the general anesthetic used in traditional approaches. This reduces risks of fully sedating the patient. Moreover, this technique is easier to perform than the current available standard methods, making it the preferred procedure by both patients and operators.

The claimed invention includes a catheter with a cutting device at its distal end. The cutting device has an outer shell with a void and a plurality of holes disposed at its distal end. A tubular blade is slideably disposed within the outer shell and has a void with a similar shape to the void of the outer shell. Both voids are aligned when the tubular blade is in a repose position. To prevent unwanted movement of the tubular blade, a spring holds the blade in place. The blade is moved via wires outside the body. The wires not only work to slide the blade but also transfer electrical information to prevent bundle branch damage and can transmit current for coagulation at the myectomy site to prevent fistulas which is a complication of surgical treatment. The proximal opening of the catheter has a blood and tissue collection bottle which is attached to wall suction.

In operation, the cutting device is positioned adjacent to the myocardium that is to be excised. Teeth located on the outer shell where the septum first contacts the device hold the tissue in place before the tubular blade starts cutting. The operator then slides the tubular blade within the outer shell to resect the septum.

BRIEF DESCRIPTION OF THE DRAWINGS

For a complete understanding of the invention, reference should be made to the following detailed description and the accompanying drawings listed below.

DETAILED DESCRIPTION OF THE PREFERRED EMBODIMENT

Figure 1:
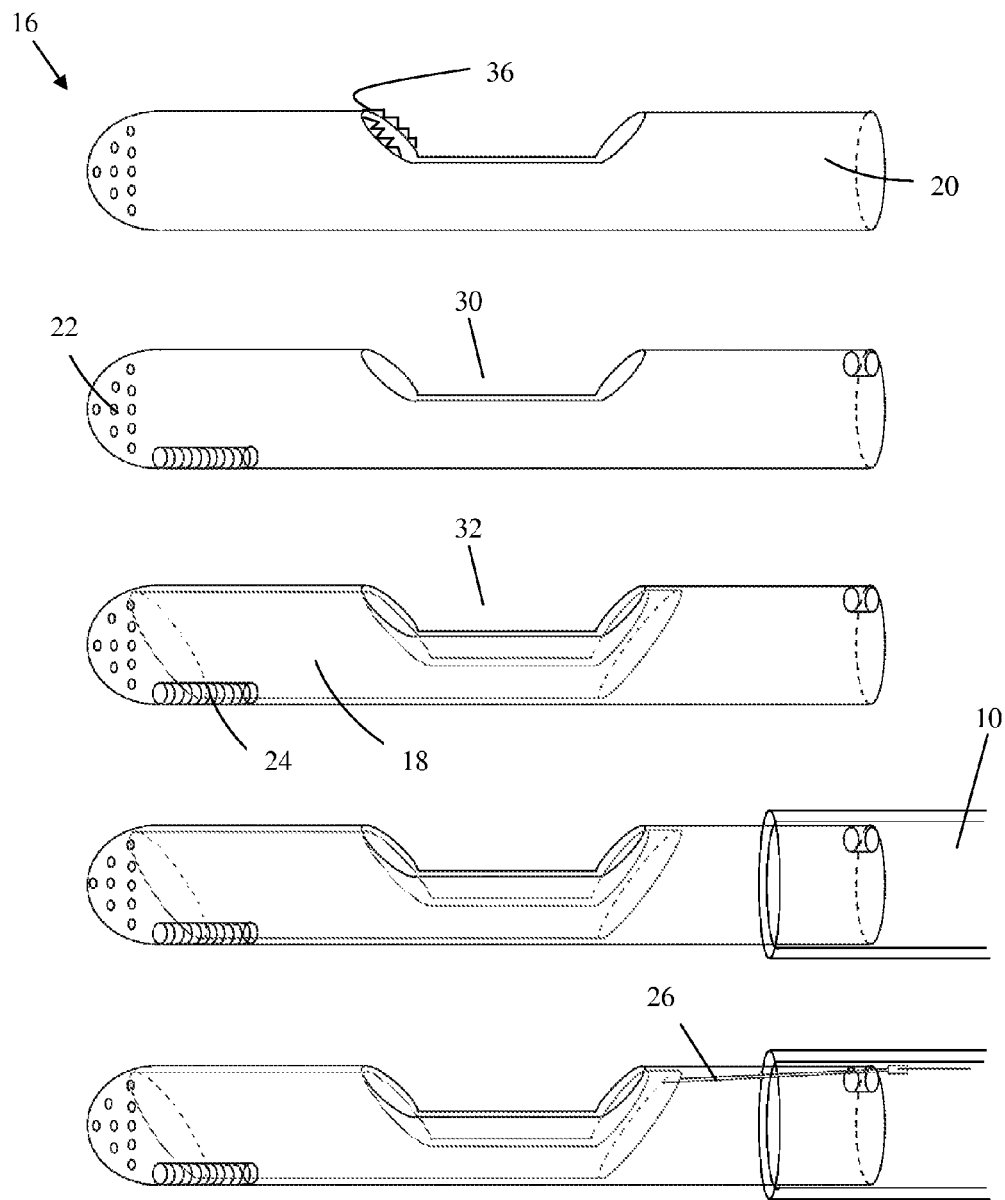
FIG. 1 is a close up illustration of the tip of the device.

The device, as collectively illustrated in FIGS. 1-4, includes a catheter 10 comprised of polyethylene or other plastic materials. The catheter 10 has proximal and distal openings. The distal end is equipped with special cutting tip 16. The cutting tip 16 has an outer shell 20 with a void 30 and a plurality of holes 22 disposed at its distal end. A tubular blade 18 is slideably disposed within the outer shell 20 and has a void 32 with a similar shape to the void of the outer shell 20. Both voids are aligned when the tubular blade is in a repose position. Both voids 30 and 32 are aligned when the tubular blade is in a repose position. A plurality of grasping teeth 36 is disposed on the distal end of outer shell void 30. The plurality of holes 22 allows blood to flow through the device and permits blood to remove tissue incised by the tubular blade 18.

The tubular blade 18 is slideably disposed inside the outer shell 20 with at least one spring 24 attached to the distal end of the tubular blade 18 to prevent unwanted movement of the tubular blade 18. When the device is in a repose position, the spring 24 is in a relaxed state; conversely, when the tubular blade 18 is deployed, the spring 24 is in a taut position. Two wires 26 are secured to the proximal end of the tubular blade 18 and allow the tubular blade 18 movement by proximal action outside the body, such as by attaching the proximal end of the wires 26 to an endoscopic instrument 34. Alternatively, the forward and backward motion of the blade can be replaced by rotating or a side-to-side movement.

The wires 26 may also transfer electrical information to the device user, thereby preventing bundle branch damage. In addition, these wires 26 can transmit current for coagulation at the myectomy site to prevent fistulas which is a complication of surgical treatment. The proximal end of the device may be attached to a blood and tissue collection bottle (not shown) which is attached to wall suction.

A plurality of grasping teeth 36 is located on the outer shell 20 where the septum first contacts the device. The teeth hold the tissue in place before the tubular blade starts cutting. The plurality of teeth may be any serration-type shape and disposed at any angle along the distal edge of the outer shell void 30, as shown in FIG. 1. The teeth secure the device in place prior to resection of the tissue.

Example 1

Method of Performing a Myectomy Using the Device

Figure 2:
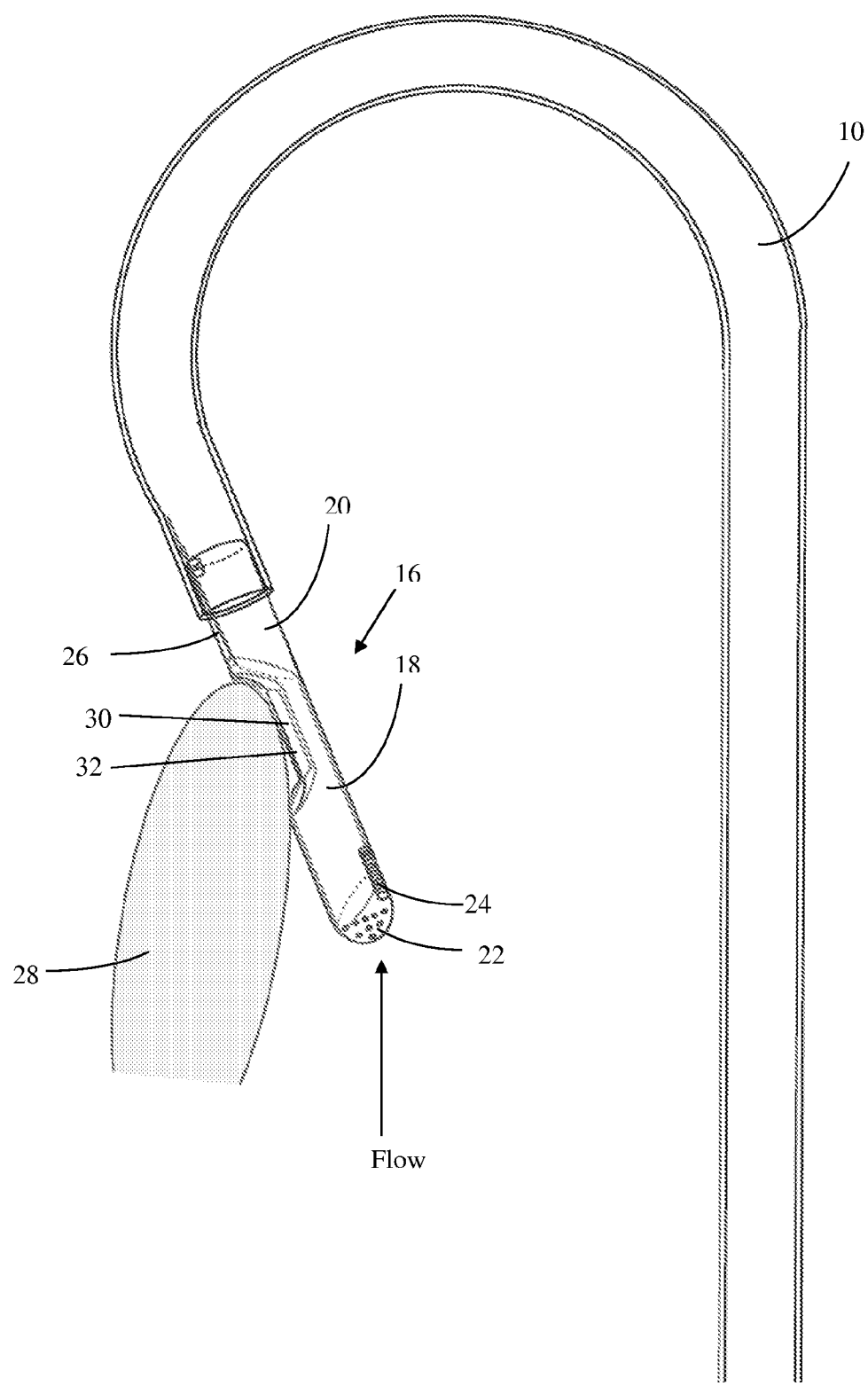
FIG. 2 is an illustration of the device in use on myocardial tissue.
Figure 3:
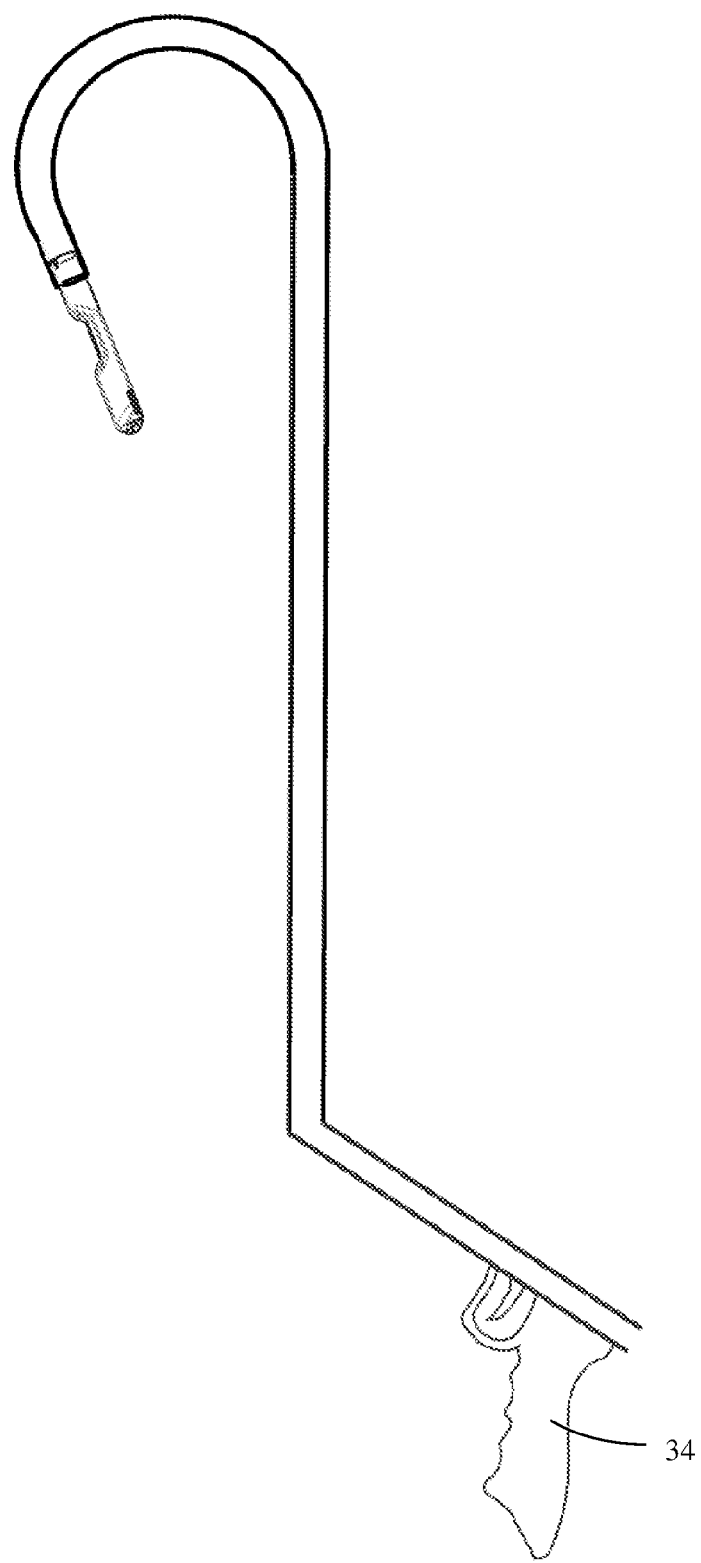
FIG. 3 is an illustration of the device, assembled with an endoscopic armature and curved for use within a patient.
Figure 4:
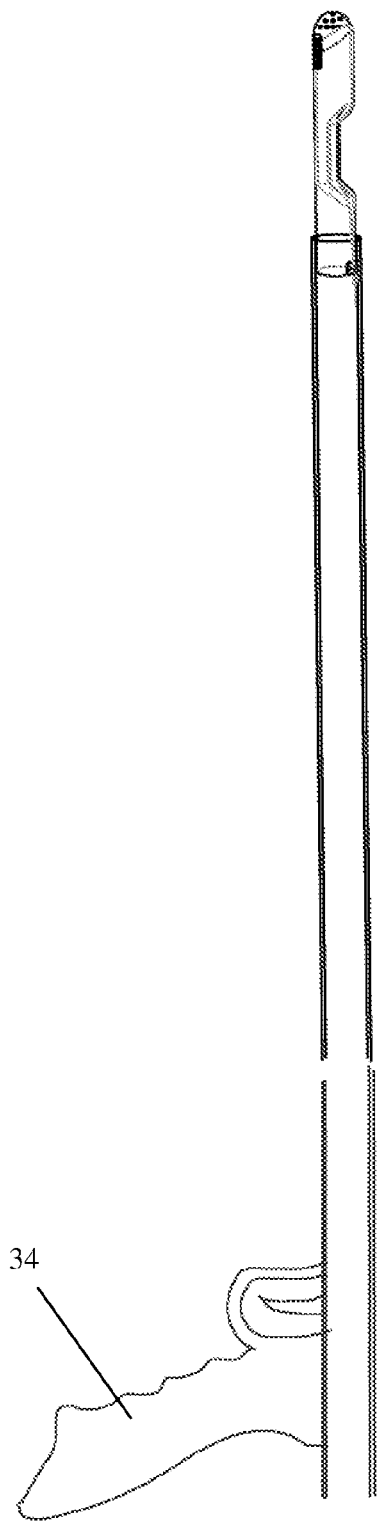
FIG. 4 is an illustration of the device, assembled with an endoscopic armature outside of the patient's body.

The femoral or brachial artery is punctured, providing access to the aorta (blood vessel). The sheath is inserted for secure hemostasis and a guide wire is advanced into the left ventricle via trans-aortic route. The device is then filled with normal saline to prevent an air embolism, and the device is then threaded via a hole at the distal end and advanced up to the left ventricle. The cutting tip 16 is positioned adjacent to the myocardium 28 that is to be excised, as seen in FIG. 2, under the guidance of transesophageal, transthoracic, or intracardiac echocardiography, and/or fluoroscopic guidance, then the guide wire is removed. After confirming the position of the cutting tip 16, the operator slides the tubular blade 18 within the outer shell 20 covering to resect the septum. The tubular blade 18 action will be controlled via the proximal end which is outside the patient's body. During this procedure, the tubular blade 18 is in the close position to prevent embolism of dissected septum.

To be more precise in selecting myocardium which needs to be excised, forceps like device (not shown) can be inserted via the proximal end of the catheter. The forceps like device would grab the targeted myocardium and pull it inside the cutting tip 16 prior to the tubular blade 18 action.

As stated, the tubular blade 18 action is controlled via the proximal end of the device which is located outside the patient's body. Negative pressure is applied at the proximal end of the catheter to suction the excised myocardium through the proximal end. The excised tissue is thus removed through the catheter by suction. The resected tissue can also be removed by complete withdrawal of the instrument, clearance of the attached tissue, and repeating above steps until satisfied tissue resection is achieved. Throughout the excision, the septal myectomy is confirmed via visual examination of the collection bottle. After the procedure, blood without tissue debris can be returned to the patient to prevent blood loss.

The above steps are repeated until desired amount of the septal tissue has been resected. Where the device is equipped with a cautery device, after the target myocardium is excised, hemostasis can be achieved simultaneously with excision via blade. The catheter is then removed, followed by the sheath and hemostatsis secured.

During the procedure, the patient optionally receives anti-coagulants to prevent thromboembolism. Further, the heart's conduction system can be identified via the cutting tip to prevent left bundle branch block and other such complications. Following the procedure, the patient is observed overnight for possible routine catheterization complications.

Example 2

Method of Using the Device to Excise Tissue or Plaques

The device is also useful in removal of tissues in organs, such as where tissue needs to be removed from an organ, tumor removal, and circulatory plaque and thrombosis removal, such as deep vein thrombosis clot removal. In such instances, the device is advanced to the excision site, as described above. Once the cutting tip is adjacent to the target tissue or clot the blade is used to cut the target tissue or clot. The excised tissue is then removed from the patient via the catheter using negative pressure.

Example 3

Method of Proximal Insertion and Implementation of the Device

Under more severe conditions, the device may also be inserted more closely to the organ of targeted implementation and not threaded through distal vessels. For instance, in HCM patients who are severely obstructed, the device may be inserted between the ribs in a location near the heart (mini thoracotomy), in a manner that punctures the heart cavity. In such insertion techniques, the tubular construct connecting the device to the suction apparatus may be comprised of non-flexible polyethylene or other solid plastic material. This embodiment may also utilize a proportionally larger device fabricated in the same manner as above. Once positioned adjacent to the target tissue, the method of utilizing the device may be performed by a surgeon's hand or by a robotic device.

Example 4

Transaortic Route

The device may also be inserted via the transaortic route to the organ of targeted implementation. Once the device is positioned adjacent to the target tissue, and the tissue is then excised as discussed above.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method for the treatment of hypertrophic cardiomyopathy, comprising the steps of:
    puncturing an artery selected from the group consisting of a femoral artery or a brachial artery;
    inserting a sheath into said puncture;
    threading a guide wire through said sheath into a left ventricle of a heart;
    threading a device through said sheath into said left ventricle of said heart, wherein said device comprises:
        a catheter having a proximal opening and a distal opening,
        a cutting device disposed at the distal opening of said catheter, said cutting device having an outer shell, said outer shell having a void, said outer shell having a plurality of holes disposed at a distal end, and
        a tubular blade slideably disposed within said outer shell, said tubular blade having a void of similar shape to said void of said outer shell, said void of said tubular blade being aligned with said void of said outer shell;
    positioning said cutting device adjacent to a myocardium needing to be excised; and
    sliding said tubular blade to excise said myocardium.

2. A method for the treatment of hypertrophic cardiomyopathy as in claim 1, further comprising the step of:
    positioning said cutting device adjacent to said myocardium using transesophageal echocardiography, transthoracic echocardiography, intracardiac echocardiography and/or fluoroscopic guidance.

3. A method for the treatment of hypertrophic cardiomyopathy as in claim 1, further comprising the step of:
    controlling said tubular blade action outside a patient's body.

4. A method for the treatment of hypertrophic cardiomyopathy as in claim 1, further comprising the step of:
    providing an anticoagulate.

5. A method for the treatment of hypertrophic cardiomyopathy as in claim 1, further comprising the step of:
    filling said device with saline.

6. A method for the treatment of hypertrophic cardiomyopathy as in claim 1, further comprising the step of:
    ensuring that said tubular blade is in a close position after tissue resection to prevent embolism of said dissected septum.

7. A method for the treatment of hypertrophic cardiomyopathy as in claim 1, further comprising the step of:
    confirming the septal myectomy excision by visually examining the collection bottle.

8. A method for the treatment of hypertrophic cardiomyopathy as in claim 1, further comprising the step of:
    removing said guide wire after positioning said cutting device adjacent to said myocardium needing to be excised.

9. A method for the treatment of hypertrophic cardiomyopathy as in claim 1, further comprising the step of:
    inserting a grabbing device through said proximal opening of said catheter to grab said myocardium needing to be excised prior to said tubular blade excising said myocardium.

10. A method for the treatment of hypertrophic cardiomyopathy as in claim 1, further comprising the step of:
    suctioning said myocardium proximally out of said catheter after said myocardium is excised by said tubular blade.

* * * * *